(12) United States Patent
Dunki-Jacobs et al.

(10) Patent No.: US 11,833,326 B2
(45) Date of Patent: Dec. 5, 2023

(54) FLUID FLOW CONTROL VALVE AND FLOW CONTROL DEVICES AND METHODS EMPLOYING SAME

(71) Applicant: Enable Injections, Inc., Cincinnati, OH (US)

(72) Inventors: Adam Dunki-Jacobs, Cincinnati, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 136 days.

(21) Appl. No.: 17/319,303

(22) Filed: May 13, 2021

(65) Prior Publication Data
US 2021/0260282 A1 Aug. 26, 2021

Related U.S. Application Data (62) Division of application No. 15/745,617, filed as application No. PCT/US2016/036445 on Jun. 8, 2016, now Pat. No. 11,033,680.

(Continued)

(51) Int. Cl.
*A61M 39/24* (2006.01)
*A61M 5/148* (2006.01)
(Continued)

(52) U.S. Cl.
CPC ...... *A61M 5/16818* (2013.01); *A61M 5/1486* (2013.01); *A61M 5/152* (2013.01);
(Continued)

(58) Field of Classification Search
CPC ............ A61M 39/26; A61M 2039/263; A61M 2039/267; A61M 5/16818; A61M 39/24;
(Continued)

(56) References Cited

U.S. PATENT DOCUMENTS 11,033,680 B2 * 6/2021 Dunki-Jacobs ......... F16K 7/075
2002/0117214 A1 8/2002 Tucker et al.
(Continued)

FOREIGN PATENT DOCUMENTS

DE 29606169 U1 6/1996
GB 1349898 4/1974
(Continued)

OTHER PUBLICATIONS

European Patent Office, Office Action for corresponding European application No. 16828176.4 (dated Nov. 15, 2022), (7 pages).
(Continued)

*Primary Examiner* — Shefali D Patel
*Assistant Examiner* — William R Frehe
(74) *Attorney, Agent, or Firm* — Cook Alex Ltd.

(57) ABSTRACT

A fluid flow control valve includes a valve body with a fluid flow lumen therethrough and a valve member located within the fluid flow lumen. At least one of the valve body and the valve member is resilient and respectively sized for movement between a normally closed position in which the valve member and a fluid lumen surface are in sufficient annular contact to block fluid flow through the fluid flow lumen and an open position in which at least one of the valve body and the valve member flexes to a spaced apart position that allows the fluid flow between the valve body and the valve member. Downstream fluid pressure may contact the valve body to enhance sealing. A fluid absorbent member may also be employed with the valve body. Flow control devices, such as medical fluid injection devices, and methods may employ the valve.

6 Claims, 9 Drawing Sheets

Related U.S. Application Data (60) Provisional application No. 62/193,899, filed on Jul. 17, 2015.

(51) Int. Cl.

| | | |
|---|---|---|
| *A61M 5/152* | (2006.01) | |
| *A61M 5/168* | (2006.01) | |
| *A61M 5/178* | (2006.01) | |
| *A61M 5/20* | (2006.01) | |
| *F04B 43/08* | (2006.01) | |
| *F04B 53/10* | (2006.01) | |
| *F16K 7/07* | (2006.01) | |

(52) U.S. Cl.
CPC ........ *A61M 5/168* (2013.01); *A61M 5/16804* (2013.01); *A61M 5/16813* (2013.01); *A61M 5/16881* (2013.01); *A61M 5/178* (2013.01); *A61M 5/20* (2013.01); *A61M 39/24* (2013.01); *F04B 43/08* (2013.01); *F04B 53/1002* (2013.01); *F04B 53/1075* (2013.01); *F16K 7/075* (2013.01); *A61M 2039/242* (2013.01); *A61M 2039/248* (2013.01); *A61M 2039/2433* (2013.01); *A61M 2039/2473* (2013.01); *A61M 2205/0216* (2013.01); *A61M 2205/7536* (2013.01)

(58) Field of Classification Search
CPC .......... A61M 5/16804; A61M 5/16881; A61M 2039/2473; A61M 2039/248; A61M 2039/2433; A61M 2039/242; A61M 5/1486; A61M 2205/0216; A61M 2205/7536; A61M 5/168; A61M 5/16877; A61M 39/22; A61M 39/227; F04B 43/08; F04B 53/1002; F04B 53/1075; F16K 7/075
See application file for complete search history.

(56) References Cited

U.S. PATENT DOCUMENTS

| | | | |
|---|---|---|---|
| 2008/0099084 A1* | 5/2008 | Headley | F04B 43/0736 137/533.15 |
| 2011/0306929 A1 | 12/2011 | Levesque et al. | |
| 2013/0345633 A1* | 12/2013 | Chong | A61M 5/145 604/134 |

FOREIGN PATENT DOCUMENTS

| | | |
|---|---|---|
| JP | S50-144319 U | 11/1975 |
| JP | 2005-523408 A | 8/2005 |
| WO | WO03/089821 A1 | 10/2003 |
| WO | WO2003/089821 A1 | 10/2003 |

OTHER PUBLICATIONS

Notification of Reasons for Refusal, counterpart Japanese App. No. 2021-078558, with English translation (dated Apr. 5, 2022) (8 pages).

* cited by examiner

FLUID FLOW CONTROL VALVE AND FLOW CONTROL DEVICES AND METHODS EMPLOYING SAME

This application is a division of U.S. application Ser. No. 15/745,617, filed Jan. 17, 2018, which is the National Stage of International Application No. PCT/US2016/036445, filed Jun. 8, 2016, which claims priority to and the benefit of U.S. Provisional Patent Application No. 62/193,899, filed Jul. 17, 2015. This application hereby incorporates by reference the entire specification, drawings and claims of each of the above applications as if they have been fully repeated herein.

The present application generally relates to flow control valves and more particularly to medical fluid transfer and/or injection devices for medical fluids that employ such valves.

BACKGROUND

Development efforts have continued in recent years in the development of new and/or improved devices for transferring, reconstituting and/or injecting medical fluids, such as drugs, antibiotics, vaccines, biologics and other medicaments for therapeutic and/or diagnostic purposes. One example of such a development may be found in PCT publication WO2014/204894 A2 by Enable Injections LLC of Franklin, Ohio USA, which is incorporated by reference herein. That publication discloses a medical fluid injection device and an associated system or device for fluid transferring, mixing, diluting and/or reconstituting a medical fluid for injection. The injection device employs an internal reservoir in the form of a resilient balloon or bladder that expands as it is filled with medical fluid from the transfer device. The injection device may, after filling, be removed from the transfer device and placed on the skin of a patient and activated. Upon activation, an injection needle is advanced from the device into the skin of the patient and the inherent pressure provided by the expanded resilient reservoir forces the medical fluid through the needle and into the patient. This injection device and others that are functionally similar may use flow control valves, such as check valves or one-way valves, to control the flow of medical fluid.

While flow control valves are, in general, well known in a wide variety of technical settings, and in a variety of configurations, there continues to be a need for new valve design and development, including, without limitation, valves particularly suited for use in medical fluid transfer and/or injection devices such as found in the above identified PCT publication. One known form of valve employs a ball within a flexible tube to control flow therethrough. Examples of these may be found in U.S. Pat. Nos. 605,693; 2,314,767; and 6,923,785; U.S. published application no. 2006/0163506: Great Britain patent application GB 2,091,853(A); and European patent application EP 0800032(A1).

SUMMARY

The present subject matter is directed to a novel flow control valve and to injection devices and/or transfer, mixing or reconstitution devices employing such a valve and to methods of their use. The following non-limiting summary is to acquaint the reader generally with various potential aspects of the present subject matter and is non-exclusive with respect to the various possible aspects or combinations of aspects found in such device or method. Additional aspects of the present subject matter may be found in the detailed description below, in the accompanying claims and/or in the accompanying figures.

In accordance with one aspect of the present subject matter, a fluid flow control valve includes a valve housing defining a valve cavity with an inlet and an outlet. A valve body having a fluid flow lumen and a valve member located within the fluid flow lumen are positioned in the valve cavity and control flow between the inlet and outlet. The valve body is resilient and the valve body and valve member are respectively sized such that the valve member is cross-sectionally larger than the fluid flow lumen when the valve body and valve member are in a substantially unstressed condition so as to result in annular contact between the valve member and valve body that substantially blocks fluid flow through the fluid flow lumen in the absence of fluid pressure from the inlet. The resiliency of the resilient valve body allows for movement between a normally closed position in which the valve member and fluid lumen surface are in contact and block flow, and an open position in response to fluid pressure from the inlet, in which the valve body flexes to allow fluid flow between the valve body and valve member. The valve body includes an exterior surface that is exposed, at least in part, to pressure from fluid between the valve member and outlet. This allows the pressure of the downstream fluid to press against the valve body and help create sealing contact against the valve member.

In accordance with another aspect of the present subject matter a medical fluid injection or transfer device may comprise a housing, a reservoir within the housing for receiving medical fluid, an inlet port in the housing for receiving medical fluid from a source, and a fluid flow path in the housing communicating between the inlet port and reservoir. The fluid flow path includes a one-way valve that includes a valve body including a fluid flow lumen therethrough and a valve member located within the fluid flow lumen. At least one of the valve body and valve member is resilient and respectively sized for movement between a normally closed position in which the valve member and a fluid lumen surface are in sufficient annular contact to block fluid flow through the fluid flow lumen in the absence of fluid pressure from the inlet port, and an open position in response to fluid pressure from the inlet port in which at least one of the valve body and valve member flexes to a spaced apart position that allows fluid flow between them.

In accordance with another aspect of the present subject matter a medical fluid injection device comprises an injection device housing, a resilient expandable reservoir within the housing for receiving medical fluid, an injection needle carried by the housing, an injection flow path for communication between the injection needle and reservoir, a port in the housing for receiving medical fluid under pressure from a source, and an inlet fluid flow path in the housing communicating between the inlet port and reservoir for introducing medical fluid into the reservoir. The inlet fluid flow path includes a one-way valve for allowing fluid flow from the inlet port into the reservoir and preventing fluid flow from the reservoir to the inlet port. The one-way valve includes a valve body including a substantially resilient sleeve portion through which inlet flow path extends, a valve inlet for fluid flow into one end of the inlet flow path and a valve outlet for fluid flow from the other end of the inlet flow path. A substantially rigid valve member is located within the inlet flow path of the resilient sleeve portion between the valve inlet and valve outlet. The valve member is sized such that it has a cross-sectional size larger than the inlet flow path in a substantially unbiased condition, such that the sleeve normally contacts the valve member and blocks fluid flow through the valve body from the reservoir to the inlet port. The sleeve is resiliently expandable under fluid pressure from the inlet port to allow fluid flow from the inlet port toward the reservoir.

In yet another aspect, a medical fluid flow control device comprises a housing, a resilient expandable reservoir within the housing, an inlet port in the housing for receiving medical fluid from a source and an outlet port in the housing for flow of fluid from the housing and a fluid flow path between the inlet port and the reservoir and between the reservoir and the outlet port. The fluid flow path between the inlet port and reservoir includes a normally closed one-way valve for allowing fluid flow from the inlet port into the reservoir and preventing fluid flow from the reservoir to the inlet port. In this aspect, the valve may have two seals or sealing areas that help prevent flow from the reservoir to the inlet port. The one-way valve includes a valve body. The valve body includes a resilient hollow sleeve portion defining a fluid flow lumen therein, a valve body inlet for fluid flow into one end of the fluid flow lumen from the inlet port and a valve body outlet for fluid flow from the other end of the fluid flow lumen into the reservoir. A substantially separate rigid valve member is located within the lumen of the resilient sleeve portion and is sized such that the valve member is larger than the lumen of the resilient sleeve when the sleeve is in an unbiased condition, whereby the sleeve portion will normally exert an annular inward force against an outer surface of the valve member to provide an annular first seal between the valve member and sleeve and block flow through the fluid flow lumen from the reservoir to the inlet port. The sleeve has an outer surface in fluid communication with the fluid flow path between the valve and reservoir and is resiliently expandable under sufficient fluid pressure from the inlet port to allow fluid flow between the valve body and valve member and into the resilient reservoir. The valve body further defines an annular valve seat in the lumen between the valve member and valve body inlet, which valve seat is contacted by the valve member in the normally closed condition to provide an additional seal against fluid flow from the reservoir. The valve member is movable away from the valve seat under fluid pressure from the inlet port to allow fluid flow through the fluid flow lumen between the valve seat and valve member.

These and other aspects of the present subject matter are set forth in the following more detailed description and accompanying figures.

DETAILED DESCRIPTION

Figure 1:
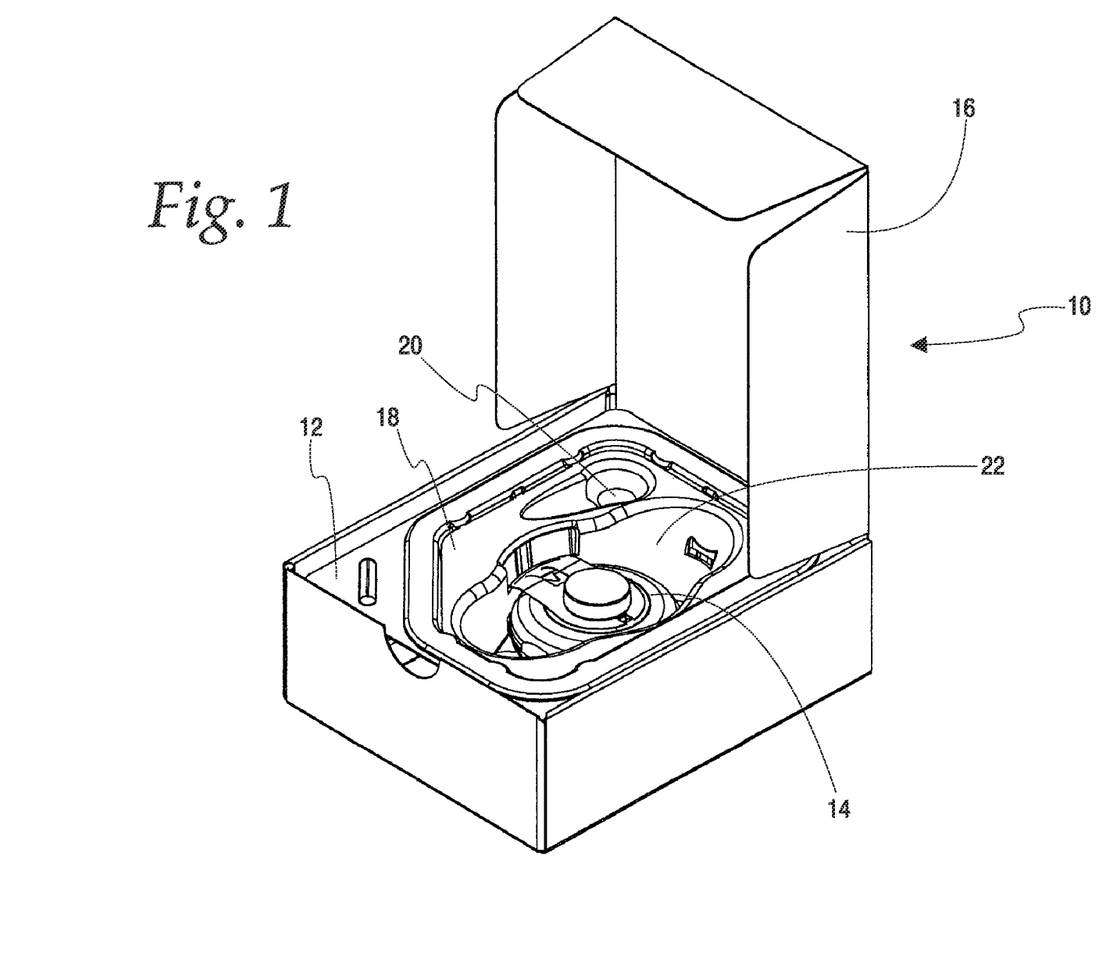
FIG. 1 is a perspective view of a transfer device and injection device combination or assembly within an outer package, which employs a flow control valve in accordance with the present disclosure.

As illustrated for purposes of explanation and not limitation, FIG. 1 depicts, in perspective view, a combined medical fluid transfer and injection device, generally at 10, in accordance with the present subject matter. The combination transfer and injection device 10 includes a transfer device or assembly 12 and an injection device or assembly 14. This combination is intended for one-time use only and is illustrated in an exemplary outer container or package 16 for shipment and/or storage.

The illustrated embodiment of the transfer device 12 allows the transfer medical fluid, which may be any injectable fluid such as for diagnostic or therapeutic purposes including, without limitation, drugs, antibiotics, chemotherapy or similar agents, biologics or other medicament, from a fluid source such as a standard syringe to the injection device 14. The transfer device includes a plastic tray 18 that has syringe receiving station or recess 20 and an injection device receiving station or recess 22. The illustrated injection device recess has a generally elongated and oval configuration that allows the user to grip and remove the injection device when needed. The particular injection device 14 is illustrated substantially as disclosed in the PCT published application incorporated by reference above, except that it employs a novel valve structure as described herein for controlling flow of fluid from the fluid source the injection device.

Figure 2:
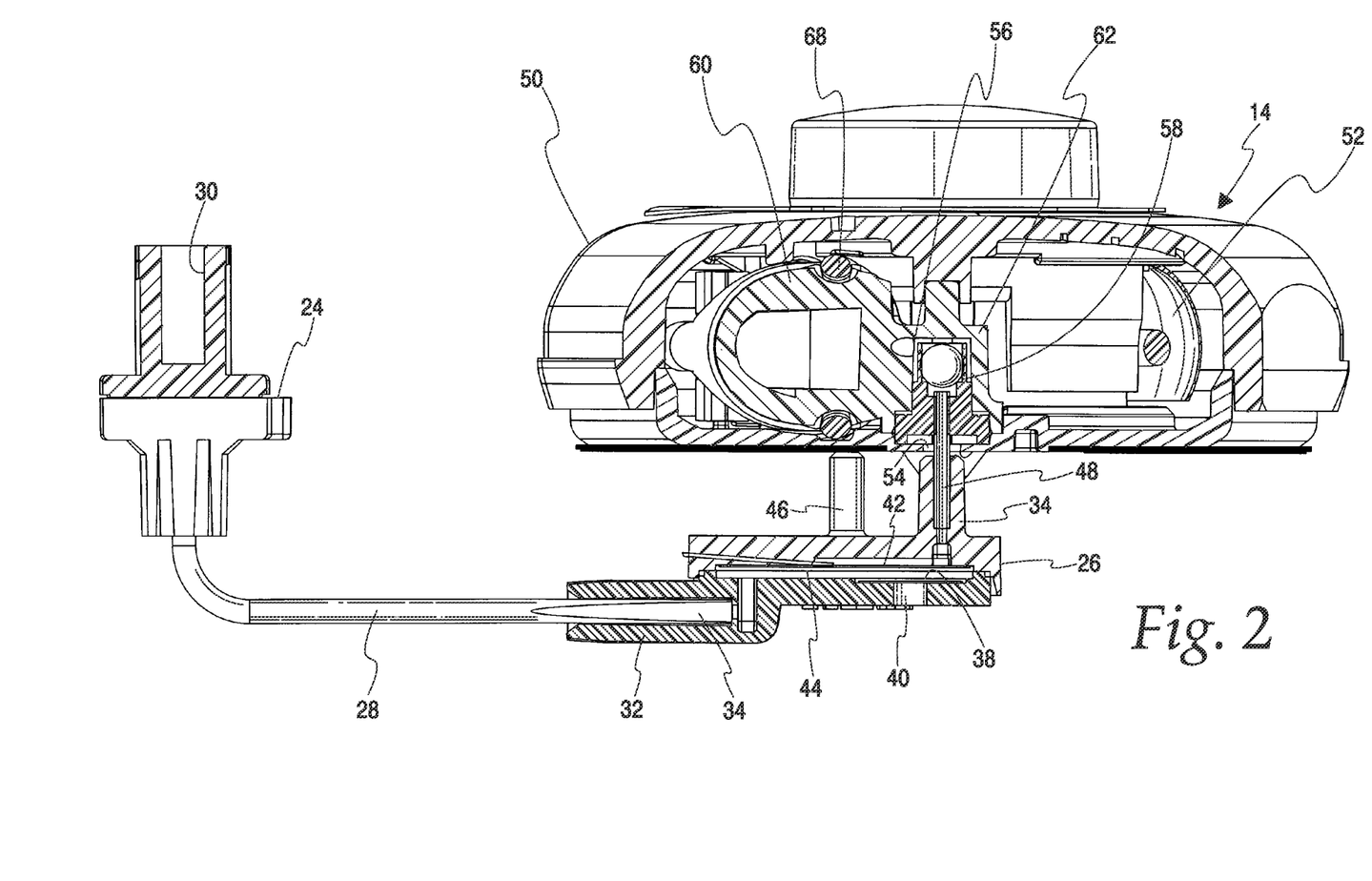
FIG. 2 is side view of the combination of FIG. 1 with the outer package removed and portions of the injection device and transfer device in sectional view for better depiction of the structures.

FIG. 2 is a side view of the transfer and injection device or combination 10 with the package 16 and tray 18 removed, and with certain parts in cross-section for clearer showing of various interior aspects. As seen in FIG. 2, the transfer device includes a first connector or port 24 for connection to a fluid source such as a syringe, a second connector port or mating member 26 for cooperation with the injection device 14 and a fluid flow path 28 connected between them. The first connector 24 is shown with the upper syringe receiving portion in section, illustrating a female luer port 30 for receiving the typical male luer end of a syringe type fluid source. The first connector has an internal passageway, not shown, that extends from the luer port 30 to the flow path 28. The fluid flow path 28 may be of any suitable construction such as flexible plastic tubing, a rigid pre-formed flow path or other. As used herein, the word, "upper," lower," "above," "below" and similar words are only indicative of relative positional relationships among various features and are not otherwise intended to impose limitations of direction.

The second connector 26 is situated in the tray 18 beneath the injection device receiving station or recess 22. The fluid flow path 28 is connected to an inlet port 32 of the second connector and an internal flow path 34 in the second connector extends from the inlet port 32 to an outlet port 36. Optionally, the internal flow path includes a hydrophobic filter such as hydrophobic membrane 38 covering a connector vent opening 40 to allow gas bubbles in the medical fluid to vent to the ambient atmosphere, while preventing liquid from flowing through the filter, and another filter such as membrane 42 through which the fluid must pass to remove particulate or other undesired materials from the fluid. The membrane 48 may have any suitable pore size and may be hydrophilic to block the passage of any gas bubbles. A membrane 42 having average pore size of about 150-170 microns may be suitable. In the illustrated embodiment, the internal flow path 34 extends through a relatively thin and wide cavity or region 44. One side of the cavity communicates through the hydrophobic membrane 38 with gas vent opening 40 in the connector wall. On the opposite side of the cavity, the membrane 42 extends over the second connector outlet port 36. The relatively thin height of the cavity promotes contact of any entrained bubbles with the hydrophobic membrane, while the relatively large cavity width provides a large cross section for fluid flow through the cavity.

The second connector 26 includes an upstanding support member 46 to help support the underside of the injection device. The outlet port 36 of the second connector also extends upwardly toward the underside of the injection device. A rigid fluid transfer tube 48 extends from the outlet port 36 for insertion into an inlet port of the injection device 14, as will be described in more detail below. The transfer tube may be made of any desired material but may preferably be of rigid plastic or metal, such as stainless steel.

The injection device 14, as noted earlier, is described for the most part in the PCT publication WO2014/204894 A2 by Enable Injections LLC of Franklin, Ohio USA, incorporated by reference herein. The injection device is intended for one-time use only, preferably for bolus injections into a patient while the device is worn by the patient. The injection device has a housing 50 that encloses a fluid reservoir, preferably a resilient, expandable reservoir such as an arcuate resilient bladder 52. The injection device housing has a fluid inlet port 54 for receiving the fluid transfer tube 48 and a fluid flow path, generally at 56, that extends between the inlet port and the reservoir. In accordance with this description, a one-way flow control valve generally at 58 is located in the fluid flow path to control fluid flow between the inlet port and the reservoir, allowing medical fluid to flow from the inlet port to the reservoir and substantially preventing fluid flow from the reservoir to the inlet port.

Figure 3:
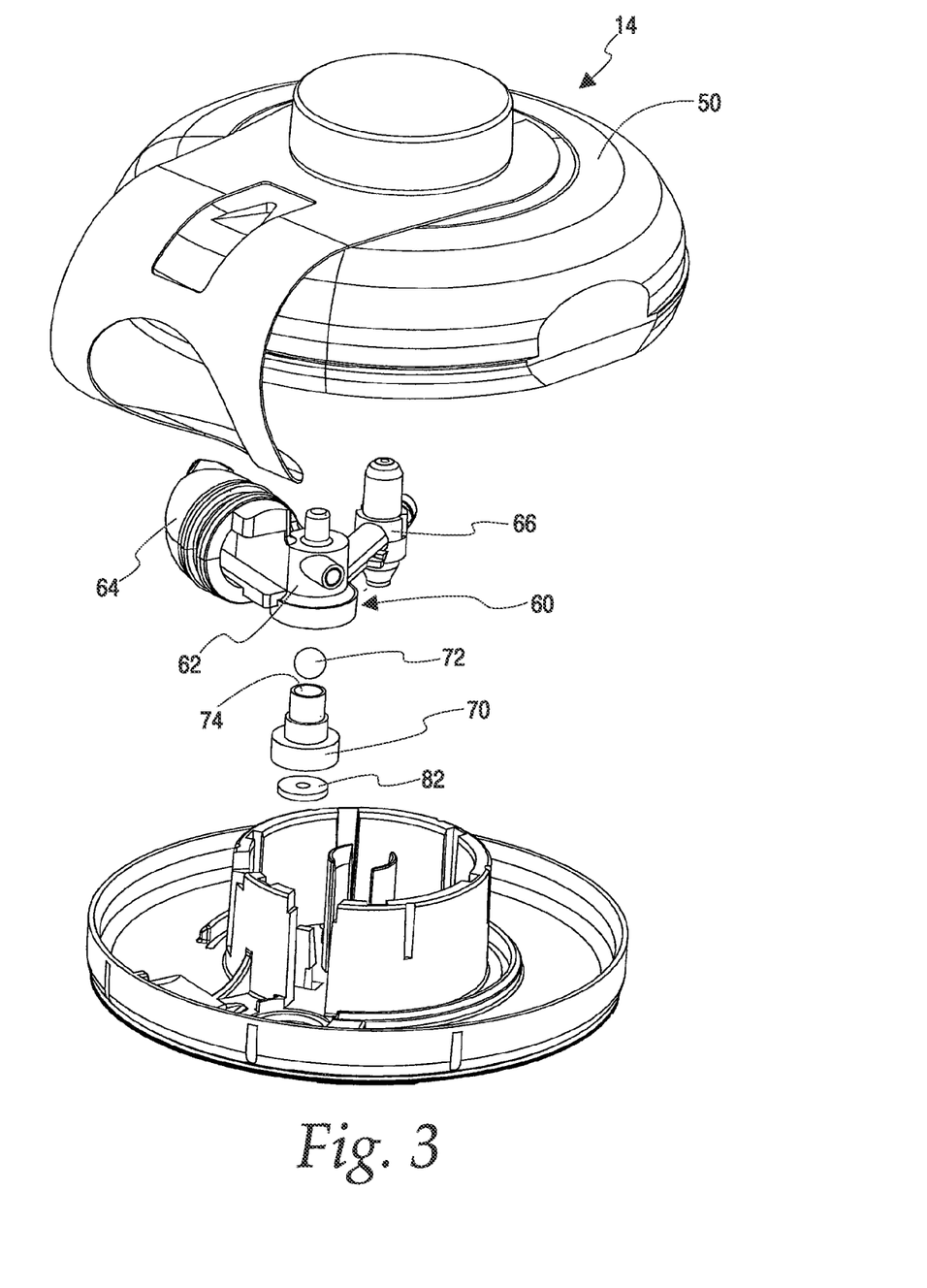
FIG. 3 is an exploded perspective view of certain parts of the injection device of FIG. 1.
Figure 4:
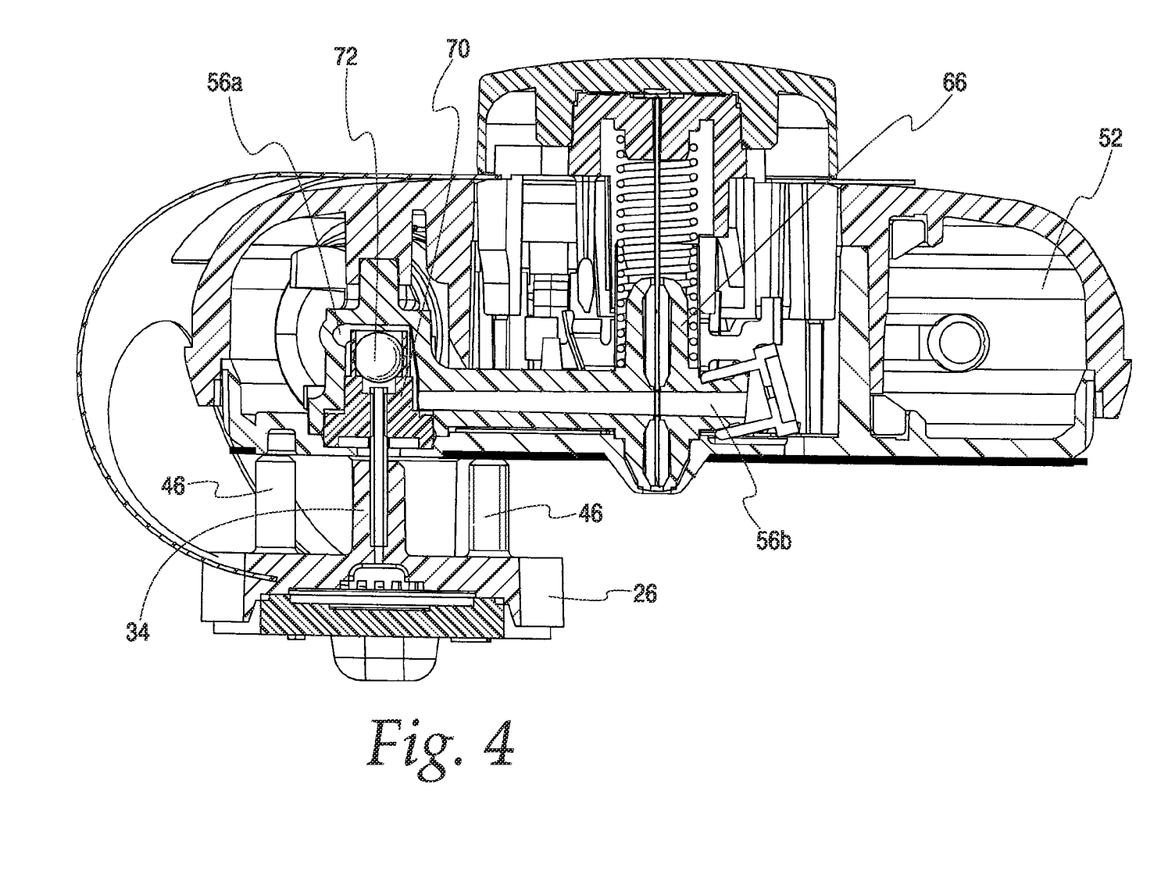
FIG. 4 is a vertical cross-sectional view of the injection device of FIG. 1 and a portion of the transfer device.

As perhaps better seen in FIG. 3, the fluid flow path 56 extends from the inlet port 54 into a manifold 60. The illustrated manifold is generally v-shaped, with a valve housing 62 at the vertex of the v-shaped manifold, a bladder mounting member 64 on one leg of the v-shaped manifold and a needle housing 66 on the other leg of the v-shaped manifold. The fluid flow path 56 extends into the valve housing 62 and branches at the valve housing and extends from the valve housing along each leg of the v-shaped manifold. This can be better seen in FIGS. 4 and 5 which show the fluid flow path branch 56a, which extends through the bladder mounting member 64, and the fluid flow path branch 56b, which extends to needle housing 66.

Figure 5:
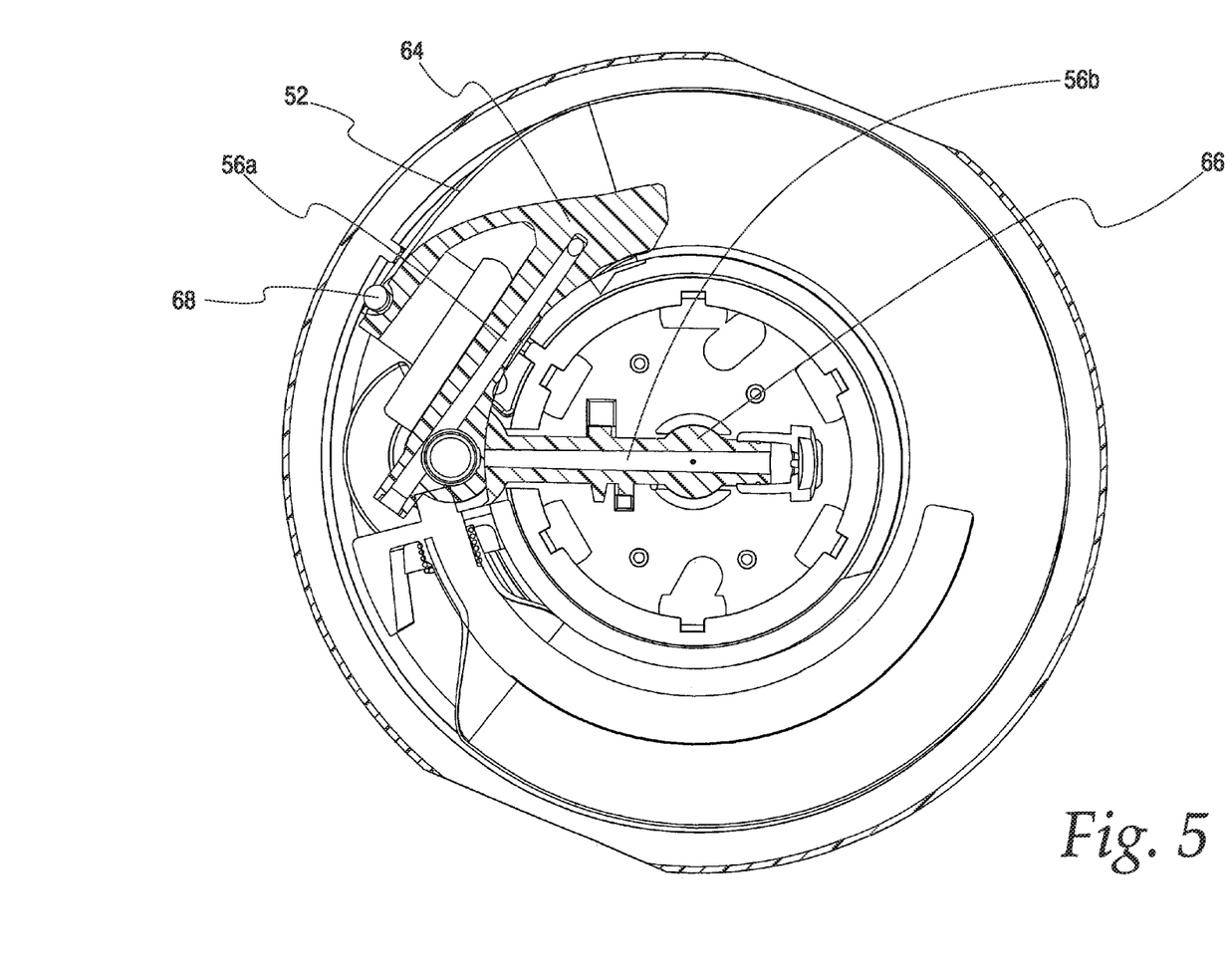
FIG. 5 is a horizontal cross-sectional view of the injection device of FIG. 1.

Referring to FIG. 5, the bladder mounting member 64 extends into an open end of an arcuate resilient bladder 52. The open end of the bladder is secured to the mounting member by a circumferential o-ring 68 that resides in a slot 70 around the mounting member and clamps the bladder wall 71 against the surface of the mounting member. The fluid flow path 56a discharges into the bladder, and FIG. 5 shows the resilient bladder as expanded after filling. When filled, the expanded resilient bladder inherently applies pressure to the fluid contained therein, and provides the motive force for expelling the fluid through an injection needle 100 (FIG. 4) when the injection device is later activated. The flow control valve 58 described below allows filling of the bladder under pressure from a medical fluid source (e.g. a syringe) and prevents the pressurized fluid in the filled bladder from escaping through the inlet port 54.

Figure 8A:
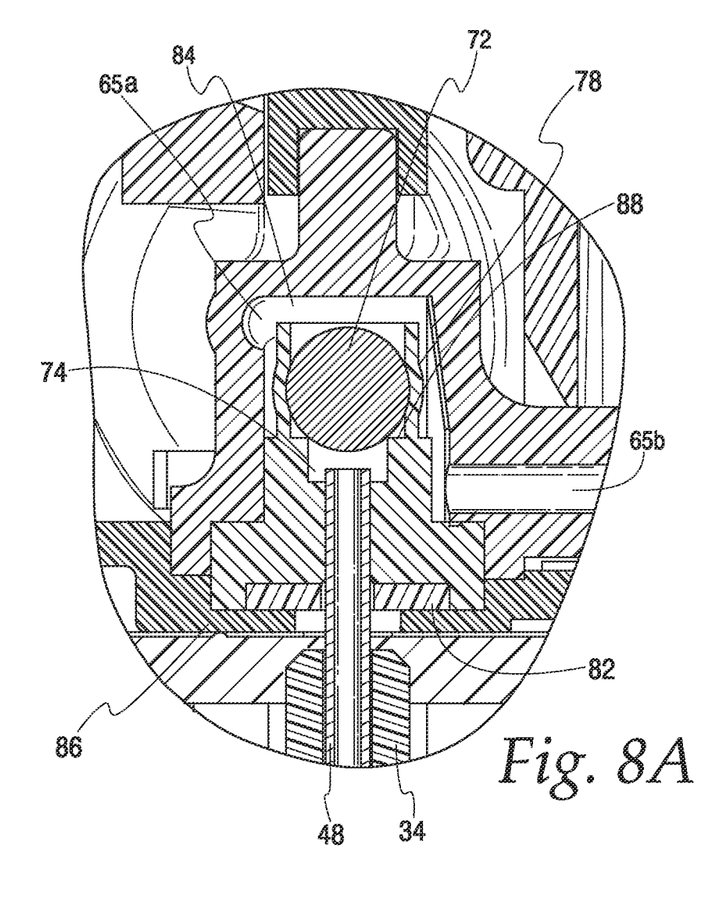
FIGS. 8A and 8B are enlarged cross-sectional views of the of the injection and transfer device combination of FIG. 2, showing the valve in closed position in FIG. 8A and in open position in FIG. 8B.
Figure 8B:
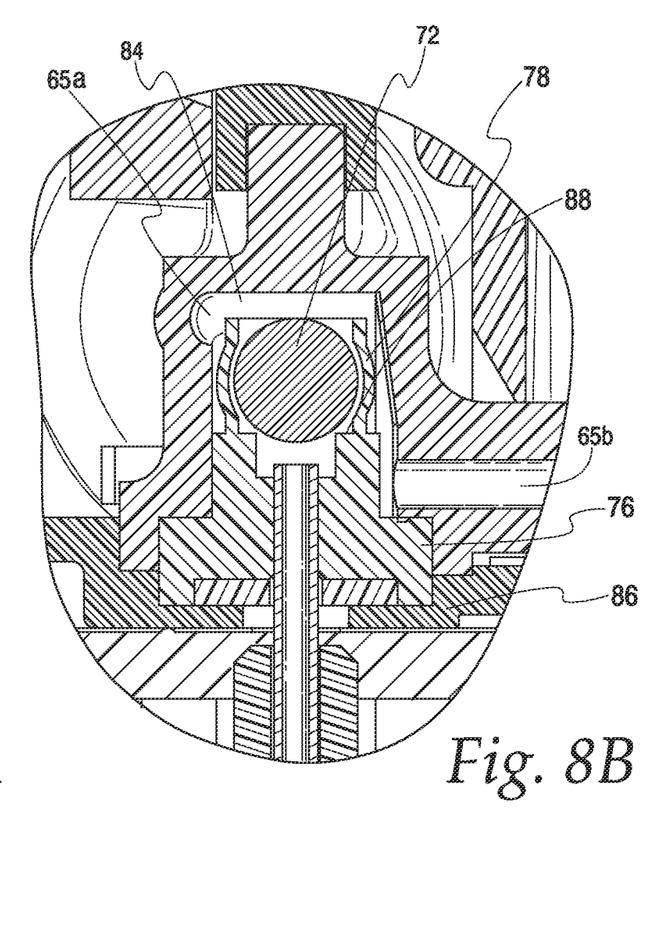

As better seen in FIGS. 2, 3, and 8, the flow control valve 58 includes a valve body 70 and a valve member 72. A fluid flow lumen 74 extends through the valve body and the valve member is located in the fluid flow lumen. At least one of the valve body and valve member is resilient and respectively sized such that the valve member 72 is cross-sectionally larger than the fluid flow lumen 74 when the valve body and valve member are in a relaxed or unstressed condition. This size relationship results in tight annular contact between the valve member and the surface of the valve body fluid flow lumen, forming what may be referred to as an annular sealing band, zone or localized stress region between the valve body and valve member, which substantially blocks fluid flow through the fluid flow lumen in the absence of fluid pressure from the inlet port. The resiliency of the valve member and/or valve body allows for movement or resilient flexing of the valve body and/or valve member between a normally closed position in which the valve member and a fluid lumen surface are in contact and blocking flow, and an open position in response to fluid pressure from the inlet port in which at least one of the valve body and valve member flexes to a spaced apart position that allows fluid flow between them.

One implementation or version of the valve body can be better seen in enlarged view, for example, in FIGS. 6-9. As shown there, the illustrated valve body includes a base portion 76 and a hollow tubular portion or sleeve 78 extending upwardly from the base portion. Fluid flow lumen 74 extends through the base and the hollow tubular portion or sleeve. The valve body also includes an exterior surface, indicated in general at 77 in FIG. 6A. The valve body may be made of any suitable material. In the illustrated version, the valve body is resilient and made of elastomeric material such as resilient polymer, and more preferably silicone material. The material of the valve body may be of selected flexibility and in one version may have a Shore A hardness of about 40 or greater. The fluid flow lumen through the base is sized to tightly and sealingly receive the fluid transfer tube 48 of the transfer device.

Figure 6A:
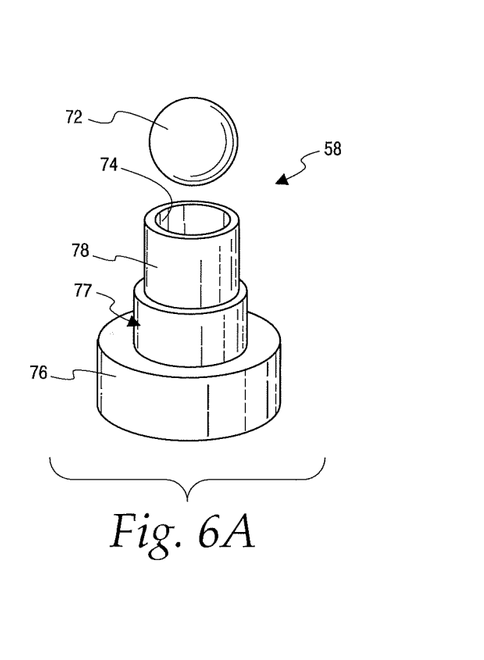
FIG. 6A is a perspective view of one embodiment of a valve body and valve member that may be employed in the injection and/or transfer device exemplified in FIG. 1.
Figure 6B:
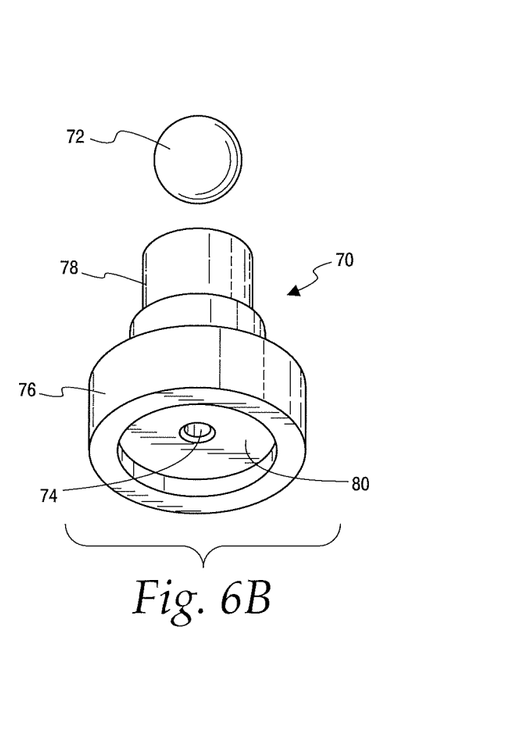
FIG. 6B is a perspective view of the embodiment of a valve body and valve member shown in FIG. 6A, taken from a different viewing angle.
Figure 7A:
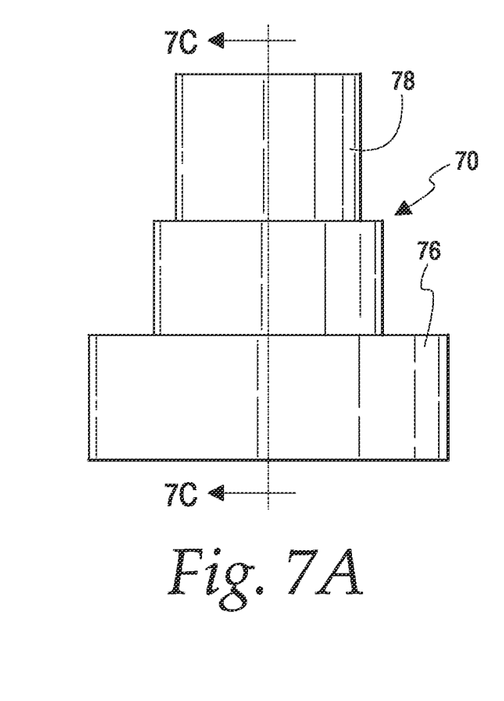
FIG. 7A is a side view of the valve body of FIG. 6A.
Figure 7B:
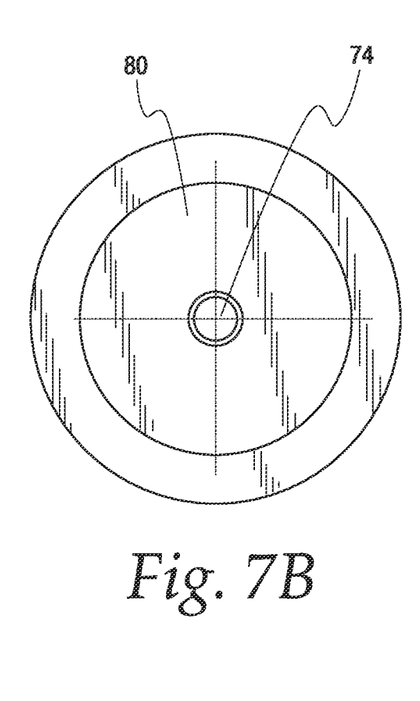
FIG. 7B is a bottom view of the valve body of FIG. 7A.
Figure 7C:
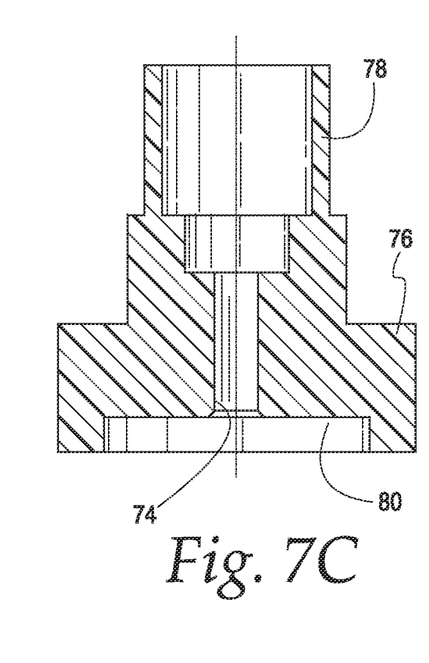
FIG. 7C is a cross-section view of the valve body of FIG. 7A, taken along line 7C-7C.

Referring to FIG. 6B, the underside of the base portion 76 optionally has a recessed area 80 around the entrance to the lumen 74 for receiving an optional fluid absorbent member 82. The fluid absorbent member may also be of any suitable material, size or shape, and in one embodiment is a cellulose disc that is affixed in the recessed area 80 to the underside of the valve body so that it is adjacent to lumen opening in the base portion and to the fluid transfer tube. The absorbent member absorbs or wicks any small residue of fluid that may escape from the lumen 74 when injection device is removed from the transfer device and the fluid transfer tube is withdrawn from the valve body.

Although either or both of the valve body 70 and valve member 72 could be resilient, in the illustrated embodiment the valve body is resilient and the valve member is rigid. In this embodiment, the valve member is spherically shaped and has a smooth outer surface for sealing contact with the wall of the fluid flow lumen 74 in the tubular portion or sleeve 78. Stainless steel is one suitable material for the valve member, and rigid plastic may also be suitable. The relative size of the valve member and valve housing may be selected to control the tension induced in the tubular portion of the valve body when the valve member is located in the fluid flow lumen 74, which affects the annular sealing pressure exerted by the tubular portion on the valve member, and therefore the amount of pressure required to open the valve.

One estimation of the pressure required to open the annular seal of fluid control valve 58 as described above is provided by the following formula:

$$P=4\pi Et(D-d)/d$$

where
E=modulus of elasticity for the valve body 70 material
d=inner diameter of the tubular portion or sleeve 78 in the relaxed, unstressed state
D=outer diameter of the spherical valve member 72
t=wall thickness of the tubular portion or sleeve 78
P=the internal pressure to open the valve.

In one particular but non-limiting example, the tubular portion of a silicone valve body, with a Shore A durometer of about 40, has a tubular portion wall thickness of about 0.011 inches (0.2 mm) and an internal fluid flow lumen diameter of about 0.108 inches (2.8 mm) in the unstressed state, with a spherical valve member having an outer diameter of about 0.118 inches (3 mm).

As an alternative to a separate valve member 72, the valve housing 62 could include a cavity extension that extends into the open end of the tubular portion 78 of the valve body and is sized (e.g. with a bulbous portion similar in shape to a spherical member) to stretch the tubular portion to provide an annular sealing zone between them, similar in function to the separate spherical valve member 72. This alternative could potentially provide cost saving and simplify assembly as compared, for example, to the use of a separate stainless steel valve member.

Turning now to FIGS. 8A and 8B, shown in enlarged detail is the flow control valve 58, valve housing 62, fluid transfer tube 48 and fluid flow path branches 56a and 56b. The valve housing defines an internal valve cavity 84 which, in this embodiment, features valve cavity outlets 65a and 65b and forms a portion of the fluid flow path 56. The flow control valve is situated within the valve cavity, with the base portion 76 fixed between the valve housing and a bottom wall 86 of the injection device housing 50, so that the tubular portion or sleeve of the valve body extends upwardly into the valve cavity. The optional absorbent member 82 is located within lower recess 80 in the valve body base, and is situated between the valve body and the inside surface of bottom wall 86. The absorbent member is therefore spaced from contact with the patient's skin by the thickness of the bottom wall.

FIG. 8A illustrates the flow control valve 58 in the injection device in the closed position. The valve is generally in this position both before and after filling of the resilient bladder 52 with medical fluid, but not during filling. In this embodiment, as described above, the spherical valve member 72 is larger than the inside diameter of the tubular portion 78 of the valve body 70. The tension induced in the resilient sleeve causes the lumen 74 surface in the tubular portion to seal against the annular surface of the valve member as described above.

FIG. 8A also shows an additional and optional aspect of the present subject matter. An optional additional or supplemental seal may be provided in the flow control valve 58 to better assure that medical fluid does not leak from the reservoir to the inlet port 54 after filling. More specifically, the valve body 70 may have an additional internal annular valve seat that engages the valve member in the closed position. One example of such a seat is illustrated in FIG. 8A in the form of an annular radial shoulder 88 located between the base portion 76 and tubular portion 78. In this embodiment the spherical valve member also contacts the internal shoulder 88 in the valve closed position, providing additional resistance to leakage from the reservoir.

As visible in the figures, in this implementation of the flow control valve, the valve cavity 84 is larger than the tubular portion 78 of the valve body 70 so that fluid in the flow path 56 can flow around at least part of the outer surface of the valve body. This allows medical fluid to flow from the reservoir through branch 56a, through the valve cavity 84 and into branch 56b to the injection needle. This also contributes to a seal between the valve member and valve body, as will be described in more detail below with respect to FIG. 9.

FIG. 8B is an illustration of the flow control valve 58 during filing of the reservoir. Medical fluid flows under pressure from a fluid source, such as a syringe, into the fluid transfer tube 48 and into fluid flow lumen 74 in the valve body 70. The pressure of the fluid lifts the valve member 72 away from annular shoulder 88 (if optionally employed) and causes the resilient tubular portion 78 to flex radially outwardly and provide a space between the valve member and surface of fluid flow lumen 74, allowing fluid to flow from the fluid transfer tube through branch 56a and into the reservoir. It should be noted that before the injection device is activated, the injection needle lumen is not open to the flow path branch 56b and thus fluid flowing into the injection device largely flows into the reservoir. The valve cavity is dimensioned or tolleranced such that the valve member 72 cannot be pushed out of the open end of tubular portion 78 of the valve body 70 by the incoming fluid. When the filling is complete and the pressure from the fluid source (e.g., syringe) is less than the opening pressure for the valve, the valve automatically and inherently returns to the closed position. Although the pressure of the filled reservoir is enough to force medical fluid through an injection needle when the injection device is eventually actuated, it is not large enough to open the valve. The medical fluid is retained in the reservoir until the injection device is needed, and the flow control valve prevents leakage to the inlet port 54.

When the injection device 14 is removed from the transfer device 12, the fluid transfer tube 48 is withdrawn from the base of the valve body 70. A very small amount of fluid may be present below the valve member and, if so, this fluid will be absorbed by the absorbent member 82, which is adjacent to the fluid inlet port 54 and spaced by the thickness of the bottom wall 86 of the injection device housing 50 from direct contact with the patients skin.

Figure 9:
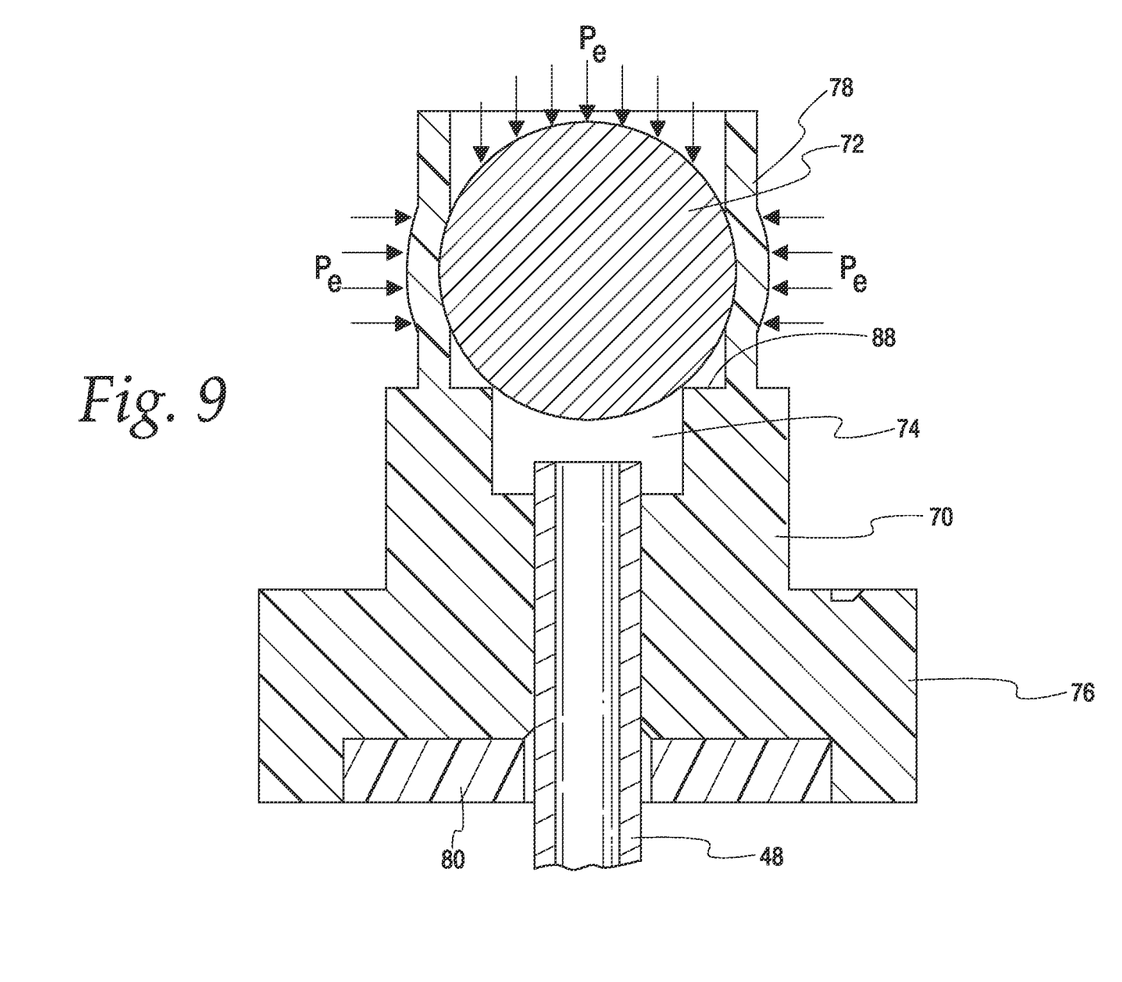
FIG. 9 cross-sectional views similar to FIG. 8A with certain parts of the injection or transfer device removed, and diagrammatically showing the fluid forces acting on the valve after the injection device is filled and before administration to a patient.

FIG. 9 diagrammatically illustrates the forces acting on the flow control valve 58 after the injection device has been filled and before it has been actuated for injection into a patient. At this point in its use, the expanded resilient reservoir exerts an expulsion pressure Pe on the medical fluid in the reservoir and in fluid flow path 56, which includes the valve cavity 44. Because the medical fluid source is no longer exerting any fill pressure, the pressure at the fluid inlet port may be assumed to be at atmospheric pressure. The valve cavity being larger than the tubular portion of the valve body, medical fluid pressure Pe is exerted against the outer surface of the tubular portion and against the exposed upper surface of the valve member 72 as shown. The pressure against the outside of the resilient tubular portion 78 adds to the inherent resilient force of the tubular portion in forcing the surface of lumen 74 against the surface of the valve member 72, enhancing the seal therebetween. Also, for valves having the optional secondary seal of the valve member against internal valve seat, such as shoulder 88 of the valve body, the fluid pressure Pe exerted against the exposed surface of the valve member helps to force the valve member against the valve seat to enhance the secondary seal therebetween.

When the injection device is activated and the injection needle is deployed into the patient's skin, the inlet port of the injection needle is open to flow path branch 56b, and reservoir pressure Pe expels fluid from the reservoir through the needle and, into the patient.

Additional Aspects

Without limiting or detracting from the foregoing description, additional features, embodiments or aspects of the present subject matter include:

Aspect 1. A fluid flow control valve including: a valve housing defining a valve cavity having an inlet and outlet, a valve body disposed in the valve cavity between the inlet and outlet and having a fluid flow lumen, a valve member located within the fluid flow lumen of the valve body, the valve body being resilient, and the valve body and valve member being respectively sized such that the valve member is cross-sectionally larger than the fluid flow lumen when the valve body in a unstressed condition so as to provide annular contact between the valve member and valve body, the annular contact substantially blocking fluid flow through the fluid flow lumen in the absence of fluid pressure from the inlet, the resiliency of the resilient valve body allowing for flexing between a normally closed position in which the valve member and a fluid lumen surface are in contact and blocking flow, and an open position in response to fluid pressure from the inlet in which at least one of the valve body and valve member flexes to a spaced apart position that allows fluid flow between them, and the valve body including an exterior surface exposed at least in part to pressure from fluid downstream of the valve body so as to encourage sealing contact between the valve body and valve member.

Aspect 2. The fluid flow control valve of aspect 1 in which valve body includes a base portion carried by the housing and hollow sleeve extending from the base portion, the interior of the sleeve defining the fluid flow lumen, a fluid orifice in the base portion communicating with one end of the sleeve and the fluid inlet port, the other end of the sleeve being open and communicating with the outlet, the valve member being disposed in the sleeve.

Aspect 3. The fluid flow control valve of aspect 1 or 2 further comprising a fluid absorbent member adjacent to the valve cavity inlet.

Aspect 4. The fluid flow control valve of any one of aspects 1-3 in which the valve body includes an annular valve seat in the fluid flow lumen between the valve member and inlet for engagement by the valve member to provide an additional seal against fluid flow through the lumen.

Aspect 5. The fluid flow control valve of aspect 4 in which the annular valve seat comprises a radial shoulder.

Aspect 6. The fluid flow control valve of any one of aspects 1-5 in which the valve body is made of silicone.

Aspect 7. The fluid flow control valve of any one of aspects 2-6 in which the valve member is generally spherically shaped and the fluid flow lumen in the sleeve is generally cylindrically shaped.

Aspect 8. The fluid flow control valve of any one of aspects 1-7 in which the sleeve is made of elastomeric material having a Shore Hardness A of about 40 or greater.

Aspect 9. A medical fluid injection or transfer device comprising: a housing; a reservoir within the housing for receiving medical fluid; an inlet port in the housing for receiving medical fluid from a source; a fluid flow path in the housing communicating between the inlet port and reservoir; the fluid flow path including a one-way valve, the one-way valve including: a valve body including a fluid flow lumen therethrough; a valve member located within the fluid flow lumen; and at least one of the valve body and valve member being resilient and respectively sized for movement between a normally closed position in which the valve member and a fluid lumen surface are in sufficient annular contact to block fluid flow through the fluid flow lumen in the absence of fluid pressure from the inlet port, and an open position in response to fluid pressure from the inlet port in which at least one of the valve body and valve member flexes to a spaced apart position that allows fluid flow between them.

Aspect 10. The injection or transfer device of aspect 9 in which the valve body is resilient.

Aspect 11. The injection or transfer device of aspect 9 or 10 in which the valve member is resilient.

Aspect 12. The injection or transfer device of any one of aspects 9-11 in which the reservoir comprises an expandable resilient balloon.

Aspect 13. The injection or transfer device of any one of aspects 9-12 in which valve body includes a base portion carried by the housing and hollow sleeve extending from the base portion, the interior of the sleeve defining the fluid flow lumen, a fluid orifice in the base portion communicating with one end of the sleeve and the fluid inlet port, the other end of the sleeve being open and communicating with the reservoir, the valve member being disposed in the sleeve.

Aspect 14. The injection or transfer device of any one of aspects 9-13 further comprising a fluid absorbent member adjacent to the orifice.

Aspect 15. The injection or transfer device of any one of aspects 9-14 wherein the sleeve is has an outer surface in fluid communication with the reservoir.

Aspect 16. The injection or transfer device of any one of aspects 9-15 further comprising a fluid flow manifold defining a valve body cavity containing the valve body and the valve member is defined by a portion of the manifold that extends into the fluid flow lumen.

Aspect 17. The injection or transfer device of any one of aspects 9-16 in which the valve body includes an annular valve seat in the fluid flow lumen between the valve member and inlet port for engagement by the valve member to provide a secondary seal against fluid flow from the reservoir toward the inlet port.

Aspect 18. The injection or transfer device of any one of aspects 9-17 in which the valve member and valve lumen are sized such that in an unbiased condition the valve member has a larger cross-section size than the valve lumen and resilient contact between the valve member and valve lumen normally prevents fluid flow through the valve lumen.

Aspect 19. A medical fluid injection device comprising: an injection device housing; a resilient expandable reservoir within the housing for receiving medical fluid; an injection needle carried by the housing; an injection flow path for communication between the injection needle and reservoir; an port in the housing for receiving medical fluid under pressure from a source; an inlet fluid flow path in the housing communicating between the inlet port and reservoir for introducing medical fluid into the reservoir; the inlet fluid flow path including a one-way valve for allowing fluid flow from the inlet port into the reservoir and preventing fluid flow from the reservoir to the inlet port, the one-way valve including: a valve body including a substantially resilient sleeve portion through which inlet flow path extends, a valve inlet for fluid flow into one end of the inlet flow path and a valve outlet for fluid flow from the other end of the inlet flow path; a substantially rigid valve member located within the inlet flow path of the resilient sleeve portion between the valve inlet and valve outlet; and the valve member being sized such that it has a cross-sectional size larger than the inlet flow path in the unbiased condition such that the sleeve normally contacts the valve member and blocks fluid flow through the valve body from the reservoir to the inlet port, the sleeve being resiliently expandable under fluid pressure from the inlet port to allow fluid flow between the valve body and valve member.

Aspect 20. The injection device of aspect 19 in which the valve body is located in the inlet fluid flow path so as to allow fluid pressure from the reservoir to be exerted against an outer surface of the sleeve portion.

Aspect 21. The injection device of aspect 19 or 20 in which the valve body includes an internal valve seat which the valve member contacts when in the flow blocking condition, providing an additional seal against fluid flow through the reservoir toward the inlet port.

Aspect 22. The injection device of anyone of aspects 19-21 in which valve body includes a base portion carried by the housing and including a fluid inlet communicating with the fluid flow path.

Aspect 23. The injection device of any one of aspects 19-22 further comprising a fill member extending through the fluid inlet.

Aspect 24. The injection device of any one of aspect 23 further comprising a fluid absorbent member adjacent to the inlet to absorb liquid from the inlet upon withdrawal of the fill member.

Aspect 25. The injection device of ay one of aspects 19-24 in which the valve member is generally spherically shaped and the fluid flow path in the sleeve is generally cylindrically shaped.

Aspect 26. The injection device of any one aspects 19-25 in which the sleeve is made of elastomeric material having a Shore Hardness A of about 40 or greater.

Aspect 27. The injection device of any one of aspects 19-26 further comprising a fluid flow manifold defining a valve body cavity receiving the valve body and the valve member is defined by a portion of the manifold that extends into sleeve.

Aspect 28. A medical fluid flow control device comprising: a housing; a resilient expandable reservoir within the housing; an inlet port in the housing for receiving medical fluid from a source and an outlet port in the housing for flow of fluid from the housing and a fluid flow path between the inlet port and the reservoir and between the reservoir and the outlet port; the fluid flow path between the inlet port and reservoir including a normally closed one-way valve for allowing fluid flow from the inlet port into the reservoir and preventing fluid flow from the reservoir to the inlet port, the one-way valve including a valve body, the valve body including a resilient hollow sleeve portion defining a fluid flow lumen therein, a valve body inlet for fluid flow into one end of the fluid flow lumen from the inlet port and a valve body outlet for fluid flow from the other end of the fluid flow lumen into the reservoir; a substantially separate rigid valve member located within the lumen of the resilient sleeve portion; the valve member being sized such that the valve member is larger than the lumen of the resilient sleeve when the sleeve is in an unbiased condition, such that the sleeve portion normally exerts an annular inward force against an outer surface of the valve member to provide an annular first seal between the valve member and sleeve and block flow through the fluid flow lumen from the reservoir to the inlet port, the sleeve being resiliently expandable under fluid pressure from the inlet port to allow fluid flow between the valve body and valve member and into the resilient reservoir, the sleeve having an outer surface in fluid communication with the fluid flow path between the valve and reservoir; and the valve body further defining an annular valve seat in the lumen between the valve member and valve body inlet, which valve seat is contacted by the valve member in the normally closed condition to provide an additional seal against fluid flow from the reservoir, the valve member being movable away from the valve seat under fluid pressure from the inlet port to allow fluid flow through the fluid flow lumen between the valve seat and valve member.

Aspect 29. A method of controlling fluid flow employing a flow control valve comprising a resilient valve body including a fluid flow lumen therein and a rigid valve member located within the fluid flow lumen, the rigid valve member being sized larger than the valve lumen to contact the surface of the valve lumen and block flow therethrough when the valve body is in a relaxed condition, the method including: applying sufficient upstream fluid pressure in the fluid flow lumen to flex the resilient valve body to a position in which the surface of the fluid flow lumen is spaced from the valve member to allow fluid flow through the lumen; reducing the upstream pressure to allow the resilient valve body to contact the valve member; and contacting an exterior surface of the resilient valve body with downstream fluid under pressure, to assist in providing sealing contact between the surface of the fluid flow lumen and the valve member.

Aspect 30. The method of aspect 29 in which the flow control valve is located in a flow path communicating with a resilient expandable downstream reservoir, and the step of applying upstream fluid pressure includes flowing fluid through the lumen and into the downstream reservoir, the upstream fluid pressure being sufficient to expand the reservoir, the reservoir being biased by its resiliency to expel fluid under pressure.

Aspect 31. The method of aspect 29 or 30 employing the flow control valve of any one of aspects 1-8.

While the flow control valve herein is described by reference to specifically illustrated structures shown in the accompanying figures, it is understood that the present subject matter is not limited to such specific structures and has application in other forms and devices without departing from the scope of this disclosure. For this reason, reference is required to the following claims to ascertain the scope of the present subject matter.

What is claimed is:

1. A method of controlling fluid flow employing a flow control valve comprising a resilient valve body including a fluid flow lumen therein, said fluid flow lumen having an interior surface and an inlet portion, and the flow control valve further including a rigid valve member located within the fluid flow lumen, the rigid valve member being generally spherically shaped with a maximum diameter sized cross-sectionally larger than the fluid flow lumen to contact the interior surface of the fluid flow lumen and block the fluid flow therethrough when the resilient valve body is in a relaxed condition, said resilient valve body further including an annular shoulder positioned between the rigid valve member and the inlet portion of the fluid flow lumen, the method including:

applying sufficient upstream pressure in the fluid flow lumen to flex the resilient valve body to a position in which the interior surface of the fluid flow lumen is spaced from the rigid valve member to allow the fluid flow through the fluid flow lumen;

reducing the upstream pressure to provide a primary seal annular contact between the rigid valve member and the interior surface of the fluid flow lumen on both sides of the maximum diameter of the rigid valve member; and contacting an exterior surface of the resilient valve body, where the exterior surface is external to the fluid flow lumen, with a downstream fluid under pressure, to assist in providing the primary seal annular contact between the interior surface of the fluid flow lumen and the rigid valve member and a supplemental seal between the annular shoulder of the resilient valve body and the rigid valve member, where the supplemental seal is separate and distinct from the primary seal and is formed primarily by the pressure from the downstream fluid of the resilient valve body and a resiliency of the resilient valve body.

2. The method of controlling the fluid flow of claim 1, wherein the flow control valve further includes a valve housing defining a valve cavity having an inlet and an outlet with the resilient valve body being disposed in the valve cavity between the inlet and the outlet.

3. The method of controlling the fluid flow of claim 2 in which the resilient valve body includes a base portion and a hollow sleeve extending from the base portion, an interior of the hollow sleeve defining the fluid flow lumen, a second fluid flow lumen in the base portion communicating with one end of the hollow sleeve, the other end of the hollow sleeve being open and communicating with the outlet.

4. The method of controlling the fluid flow of claim 3, wherein the hollow sleeve is made of an elastomeric material having a Shore Hardness A of 40 or greater.

5. The method of controlling the fluid flow of claim 2, wherein the flow control valve further includes a fluid absorbent member adjacent to the inlet of the valve cavity.

6. The method of controlling the fluid flow of claim 1, wherein the resilient valve body is made of silicone.

* * * * *